United States Patent [19]

Ueno et al.

[11] Patent Number: 5,011,984
[45] Date of Patent: Apr. 30, 1991

[54] MANUFACTURING METHOD FOR 2-HYDROXYNAPHTHALENE-6-CARBOXYLIC ACID

[75] Inventors: Ryuzo Ueno, Nishinomiya; Yoshiyasu Masada, Hirakata; Toru Mori, Takarazuka, all of Japan

[73] Assignee: Kabushiki Kaisha Ueno Seiyaku Oyo Kenkyujo, Osaka, Japan

[21] Appl. No.: 508,530

[22] Filed: Apr. 12, 1990

Related U.S. Application Data

[63] Continuation of Ser. No. 327,515, Mar. 22, 1989, abandoned, which is a continuation of Ser. No. 76,298, Jul. 22, 1987, abandoned.

[30] Foreign Application Priority Data

Jul. 25, 1986 [JP] Japan .............................. 61-176254

[51] Int. Cl.$^5$ .............................................. C07C 51/15
[52] U.S. Cl. .................................................. 562/425
[58] Field of Search ......................................... 562/425

[56] References Cited

U.S. PATENT DOCUMENTS

| | | | |
|---|---|---|---|
| 1,593,816 | 7/1926 | Andre | 562/425 |
| 4,020,102 | 4/1977 | Quadbeck-Seeger et al. | 562/425 |
| 4,287,357 | 9/1981 | Mueller et al. | 562/425 |
| 4,329,494 | 5/1982 | Montgomery | 562/425 |
| 4,345,094 | 8/1982 | Mueller et al. | 562/425 |
| 4,345,095 | 8/1982 | Mueller et al. | 562/425 |

FOREIGN PATENT DOCUMENTS

| | | | |
|---|---|---|---|
| 1190245 | 7/1985 | Canada | 562/425 |
| 0053824 | 6/1982 | European Pat. Off. | |
| 0081753 | 6/1983 | European Pat. Off. | |
| WO81/02573 | 9/1981 | PCT Int'l Appl. | |

*Primary Examiner*—Bruce Gray
*Attorney, Agent, or Firm*—Sterne, Kessler, Goldstein & Fox

[57] ABSTRACT

The present invention provides a production of 2-hydroxynaphthalene-6-carboxylic acid improved in the yield and the selective ratio, in which β-naphthol and water formed in the reaction system are eliminated therefrom through the reaction.

8 Claims, No Drawings

MANUFACTURING METHOD FOR 2-HYDROXYNAPHTHALENE-6-CARBOXYLIC ACID

This application is a continuation of application Ser. No. 327,515, filed on Mar. 22, 1989, now abandoned, which is a continuation of Ser. No. 076,298, filed July 22, 1987, now abandoned.

BACKGROUND OF THE INVENTION

The present invention relates to an improved method of manufacturing 2-hydroxynaphthalene-6-carboxylic acid by the reaction of β-naphtholpotassim and carbon dioxide.

2-hydroxynaphthalene-6-carboxylic acid is an important raw material for every kind of aromatic polyesters and indispensable especially to the production of a liquid crystal polymer excellent in workability and fluidity, and a resin or fiber having good elasticity and heat resistivity.

There had been known many methods of production for 2-hydroxynaphthalene-6-carboxylic acid, for example, the U.S. Pat. No. 1593816 (1926), old one, and the Japanese patent KOKAI Nos. 95939/1982 and 212139/1982, relatively new disclosures.

By such known methods, however, it had not been possible to produce 2-hydroxynaphthalene-6-carboxylic acid at a high yield and at a high selective ratio of (term "selective ratio" means the ratio of 2-hydroxy naphthalene-6-carboxylic acid to (2-hydroxynaphthalene-6-carboxylic acid plus 2-hydroxynaphthalene-3-carboxylic acid) in the present specification.)

In our early researches for establishing a method of producing 2-hydroxynaphthalene-6-carboxylic acid from β-naphthol on an industrial scale, it had been found that the product was obtainable at relatively good yields and at high selective ratios when the reaction was made to take place by selecting a carbon dioxide pressure suitable for the reaction temperature as removing free β-naphthol arised therein from the reaction system by means of overflow with the reaction medium (reference: Patent Publication No. 35911/1984). It is understood that, in the above-mentioned Kolbe-Schmitt reaction, the intermediate formed by bonding of a potassium atom to an aromatic nucleus of β-naphthol is decomposed in the presence of water to return the β-naphthol. Therefore, it had been generally considered that this reaction must be carried out by first reacting β-naphthol and a potassium source in an aqueous solution, second the β-naphtholpotassium obtained therefrom is dehydrated, and third reacted with carbon dioxide. And the degree of this dehydration has been considered to bear upon the yields and selective ratios of the product.

SUMMARY OF THE INVENTION

It has been found that the yield of 2-hydroxynaphthalene-6-carboxylic acid and the selective ratio are adversely influenced by free β-naphthol, 2-hydroxynaphthalene-3-carboxylic acid produced during the reaction, and water arising from a potassium source in the reaction system (for example, see the reaction schemes (i)–(v) below) and also the residual water in β-naphtholpotassium, and found that the yield and the selective ratio can be improved, and the side reaction, such as the formation of β-naphthol dimer, condensates with naphthoic acid, tar and the like can be decreased to give the 2-hydroxynaphthalene-6-carboxylic acid in a higher yield and excellent selective ratio, if such the water is removed together with the β-naphthol from the reaction system during the reaction.

Further, it has been found that the elimination is achieved by transferring the water and the free β-naphthol together with carbon dioxide gas from the reaction system to vaper phase, but not by overflowing as a conventional method, the yield and the selective ratio can be remarkably improved, and the side reaction can be effectively prevented.

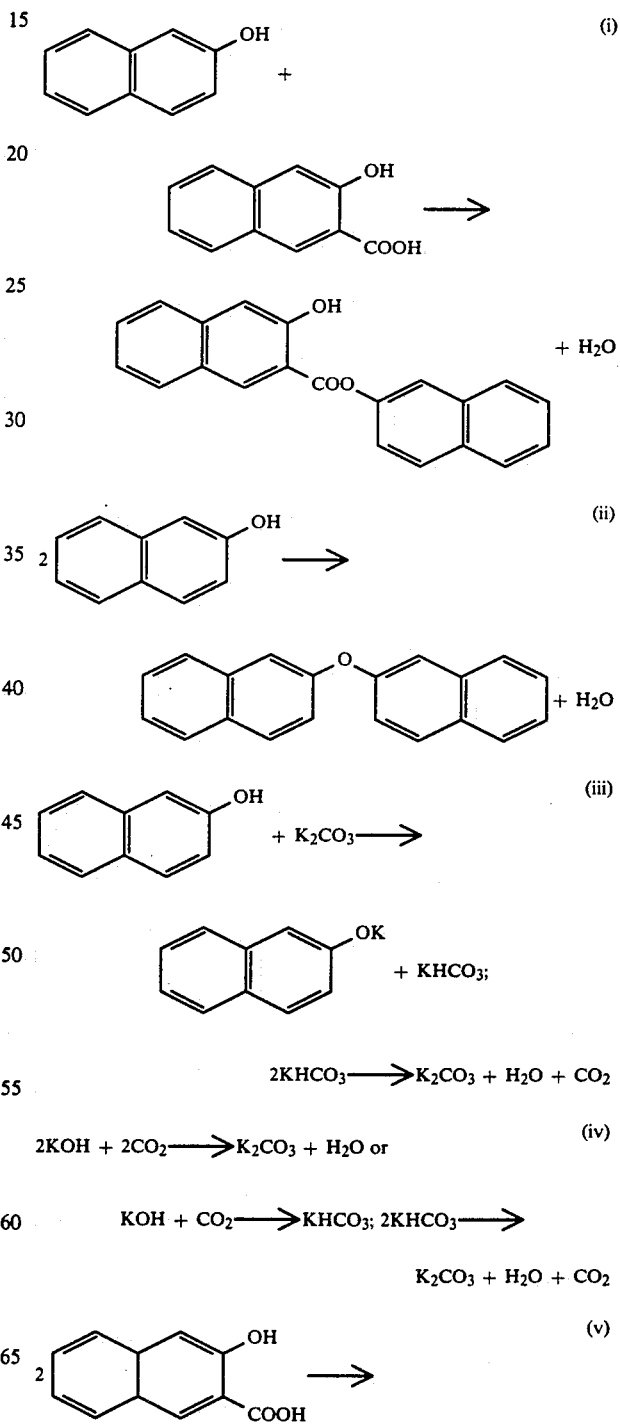

-continued

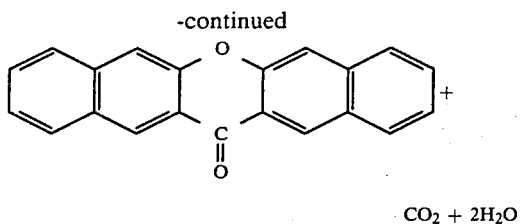

$$CO_2 + 2H_2O$$

The method according to the present invention is superior to the conventional method in which the β-naphthol is eliminated from the reaction system by the overflow for preventing the side reaction.

The present invention provides a method of preparing 2-hydroxynaphthalene-6-carboxylic acid wherein β-naphtholpotassium and carbon dioxide, in the presence of a reaction medium that substantially does not dissolve the β-naphtholpotassium under heat and pressure, are reacted with simultaneous transference of β-naphthol and water existing in the reaction system to the vapor phase and elimination thereof from the reaction system.

According to the present invention the yield of the 2-hydroxynaphthalene-6-carboxylic acid and the selective ratio can be improved.

DETAILED DESCRIPTION OF THE INVENTION

The present invention relates to a method of manufacturing 2-hydroxynaphthalene-6-carboxylic acid wherein β-naphtholpotassium and carbon dioxide, in the presence of a reaction medium that substantially does not dissolve the β-naphtholpotassium under heat and pressure, are reacted with simultaneous transference of β-naphthol and water formed in the reaction system to a vapor phase and elimination thereof from the reaction system.

According to the present invention, β-naphtholpotassium and carbon dioxide are reacted in the presence of a reaction medium that substantially does not dissolve the β-naphtholpotassium under heat and pressure.

The β-naphtholpotassium for this reaction can be prepared from β-naphthol and an alkaline potassium compound by an ordinary method and, when used, the product is required to be sufficiently dehydrated. It is preferable to employ an alkaline potassium compound such as potassium hydroxide and potassium carbonate, especially potassium hydroxide for the formation of the β-naphtholpotassium. β-Naphthol is to be employed in a quantity within the range of 0.97–1.03 mol, preferably in the vicinity of 1.00 mol, against one equivalent of an alkaline potassium compound. The β-naphthol reacts easily with an alkaline potassium compound, for instance, by the reaction of addition of β-naphthol into an aqueous solution of potassium hydroxide to give a concentrated solution of β-naphtholpotassium. Since β-naphtholpotassium must be dehydrated in this process, it is dehydrated, for example, by heating at a temperature of 240° C. or higher, preferably in the range of 250°–300° C., in a stream of an inert gas such as nitrogen and under atmospheric pressure or under a pressure somewhat increased or reduced. With the melting point at about 235° C., β-naphtholpotassium is a liquid state at the above-mentioned heating temperature range and is therefore capable of being dehydrated continuously or batchwise under the absence of a reaction medium. Such the dehydration without any medium is more advantageous because it does not need a big apparatus and a powerful energetic stirring operation that would otherwise be required to evenly mix β-naphtholpotassium with the medium large different in specific gravity.

Also, from the viewpoint of improving the yield and selective ratio of the product, the medium for the dehydration, preferably, is not used, because such disuse permits the reaction system between β-naphthol and carbon dioxide to be provided with a reaction medium at an accurate ratio and at a suitable temperature so that the heat evolved from the reaction of β-naphtholpotassium with carbon dioxide can be easily eliminated therefrom in such a manner as to achieve a satisfactory adjustment of the reaction temperature for improvement of said yield and selective ratio. But it is also practical to carry out the process of forming β-naphtholpotassium and/or its dehydration batchwise or continuously in the presence of a reaction medium.

The reaction between β-naphtholpotassium and carbon dioxide may be carried out at a reaction temperature within the range 230°–350° C., preferably within the range 40°–320° C., and under a pressure of carbon dioxide at a suitable value corresponding to the reaction temperature, but within the range of 1–20 kg/cm² (G), preferably within the range of 2–16 kg/cm² (G). The pressure of carbon dioxide can be selected preferably within a range of 2–7 kg/cm² (G) for a reaction temperature of 260° C. and within a range of 2–10 kg/cm² (G) for 280° C.

In the most preferable embodiment the carbon dioxide is dispersed into the reaction medium by, for example, such a manner that the carbon dioxide is blown through a blow nozzle with stirring. By such a dispersion of the carbon dioxide the carboxylation of β-naphthol can be accelerated; the elimination of free β-naphthol from the reaction system can be effectively achieved, and the side reaction such as a production of β-naphthol dimers, tars and the like can be reduced in comprarison with the overflow method. Therefore, the dispersion of the carbon dioxide into the reaction system is extremely effective to improve the yield of the 2-hydroxynaphthalene-6-carboxylic acid and the selective ratio.

Applicable in the practice of this invention is a reaction medium which does not dissolve β-naphtholpotassium to any substantial degree and whose specific gravity at normal temperature is within the range 0.6–1.5, preferably within the range 0.7–1.4. A reaction medium suitable for the present invention can be selected from hydrocarbons of the aliphatics, alicyclics or aromatics or ethers containing their residual radicals: namely, for example, light oil, kerosene, gasoline, lubricating oil, clean oil, alkylbenzenes, alkylnaphthalenes, diphenyls, diphenylalkanes, alkyldiphenyls, triphenyls, hydrogenated triphenyls, diphenyl ethers, alkylphenyl ethers, alkyldiphenyl ethers, etc., and their mixtures. According to the present invention a reaction medium having a boiling point within the range 150°–400° C., especially within the range 180°–400° C., is preferable.

A reaction medium normally is to be employed in a quantity which is 0.5 times that of β-naphtholpotassium or more in terms of weight, preferably within the range of 0.5–10 times and especially recommendably within the range of 1–5 times. When a reaction medium is used for the process of forming β-naphtholpotassium (a reaction between β-naphthol and an alkaline compound) and/or for its dehydration, it is preferable to employ said reaction medium in a quantity which additionally includes a portion forming an azeotrope with water.

A method embodying the present invention, in a reaction of β-naphtholpotassium with carbon dioxide in the presence of a reaction medium that substantially does not dissolve β-naphtholpotassium under heat and pressure, essentially consists of converting the β-naphthol produced together with the water existing in a system of liquid phase to the vapor phase and eliminating them from the reaction system speedily, especially under the flow of carbon dioxide.

In the practice of said manufacturing method previously developed by the same inventors as the present inventors (reference: Japanese patent publication No.35911/1984) wherein β-naphthol is eliminated from the reaction system in a manner of overflow together with the reaction medium, such as light oil, it is very difficult to eliminate the water existing in the reaction system efficiently therefrom.

As a manner of the transference of β-naphthol and water to the vapor phase and their elimination from the reaction system in the practice of this invention following manners are exemplified, but not restrictive:

(1) the gas in the reaction system is intermittently exhausted over the reaction and pressurized $CO_2$ is taken in as a replenishment;

(2) the gas in the reaction system is continuously exhausted over the reaction, as pressurized $CO_2$ is replenished so as not to allow the pressure therein to fall;

(3) the gas in the reaction system is subjected to condensation by means of a cooling pipe connected to the reaction chamber so that the liquid condensate obtained thereby is eliminated from the reaction system continuously or intermittently ($CO^2$ gas is collected and returned to the reaction chamber).

In order to transfer the β-naphthol and the water into the vaper phase and eliminate them from the reaction system efficiently and immediately, it is better to carry out the reaction of β-naphtholpotassium and carbon dioxide with sufficient stirring in the presence of the reaction medium which (i) can disperses but does not dissolve the β-naphtholpotassium at the reaction temperature, about 250°-300° C., (ii) does not have a so high vaper pressure as to remarkably increase the reaction pressure, and (iii) has no substantial influence to the reaction thereof.

This reaction can be carried out batchwise or in a continuous procedure.

In a reaction of β-naphtholpotassium with carbon dioxide in the foregoing description, it is advantageous to add about 1-1.5 equivarent of potassium source based on the free β-naphthol arising in the reaction to the reaction system. As the potassium source there are exemplified potassium carbonate, potassium bicarbonate, alkylpotassium carbonate, alkoxypotassium, alkylpotassium, and potassium sulfate. For example, the existence of such a source of potassium in a quantity approximately within the range 1-1.5 mol against free β-naphthol can reconvert the β-naphthol to β-naphtholpotassium which can react with carbon dioxide, and, moreover, as the free β-naphthol can be reduced by the reconvert, the water attributed to the β-naphthol is also reduced, so that the yield of the product can be improved. The β-naphtholpotassium and reaction medium can be more uniformly mixed under the presence of the inorganic alkaline salts and by stirring.

The finishing process, for example, can be carried out as follows. After the reaction with carbon dioxide, water is added to the mixture and its pH value is adjusted to 6.5-8 using an acid, such as sulfuric acid or hydrochloric acid, so that β-naphtholpotassium in the reaction product is liberated as β-naphthol. Before or after the above-mentioned step, the layer of reaction medium is separated and, when occasion demands, β-naphthol and the layer of tar containing resinous substances in the aqueous layer are settled in the liquid state and separated, and the tar layer separated is washed with water and the washing liquor is returned to the separated aqueous layer. Said aqueous layer is extracted by means of a hydrophobic solvent at a temperature of 110° C. or lower. Applicable to this extraction are such solvents as a hydrocarbon, a halogenated hydrocarbon, a nitrated hydrocarbon, an ether, a ketone, and an alcohol with a carbon number of four or more. Such a solvent for extraction is used in a quantity of 0.3-2 times the volume of the aqueous layer and at temperature of 30°-110° C. The β-naphthol in the layer of the reaction medium may be used without chemical change in a recycling system, or preferably used as collecting it in the form of a water solution of β-naphtholpotassium by reacting potassium hydroxide in water with the β-naphthol contained in both the layer of reaction medium and the extracted layer. The β-naphthol in the extracted layer or tar layer can also be collected by, for example, reduced pressure distillation. The aqueous solution of β-naphtholpotassium and the β-naphthol thus collected may be recycled for the continued process by returning to the step of the preparation of raw materials.

In a procedure for taking out the object substances, the water layer thus extracted is adjusted to the pH value of about 3-5, preferably about 3.5-4.5, to give 2-hydroxynaphthalene-6-carboxylic acid at high purity. If the pH of this acid-separating mother liquor is adjusted further to a value of about 1-3, preferably to a value of about 1.5-2.5, for further acid separating, 2-hydroxynaphthalene-6-carboxylic acid and 2-hydroxynaphthalene-3-carboxylic acid are obtained in the form of a mixture. These two acids can easily be fractionated by, for example, washing with an organic solvent or a mixture of an organic solvent with water. Depending on the use of the object substances, said extracted water layer may be subjected directly from the beginning to acid separating at a pH value approximately below three. The improvement of the selective ratios and the yields of the 2-hydroxynaphthalene-6-carboxylic acid in the present invention is achieved by the aforementioned simplified acid-separation.

In a reaction between β-naphtholpotassium and carbon dioxide according to the present invention, the β-naphthol which is produced during the reaction and takes its part in said various side reactions and water whose existence in the reaction system contributes to lowering the yield of the product are speedily transferred as vapors or liquid condensates and eliminated from the reaction system so that, compared with conventional methods, the reaction shows improvement not only in the yield of 2-hydroxynaphthalene- 6-carboxylic acid but also the selective ratio.

The present invention will be illustrated by the following Examples, but it should not be restricted by the Examples.

EXAMPLE 1

In a one-liter autoclave were charged a 252 g of 70% aqueous solution of β-naphtholpotassium, 26.5 g of 50% aqueous solution of potassium carbonate, and 365 g of light oil, and the charged mixture was subjected to dehydration at 260° C. for 3 hours with stirring under inert gas atomosphere. The distilled light oil is returned to the mixture. Pressure was applied to the inside of the autoclave so as to control the $CO_2$ gas pressure at 3 kg/cm$^2$ (G), as discharging the $CO_2$ gas from an outlet nozzle at the rate of 72 liter/hr, and simultaneously the β-naphthol and water in the form of gases were cooled to eliminte from the autoclave during the raction. The above reaction of the β-naphthol and $CO_2$ is continued at 260° C. about 6 hours, and the $CO_2$ is dispersed in the reaction mixture by blowing it therein from the reaction vessel with vigorous agitation.

After comfirming at light oil, β-naphthol and water were condensed in the cooling pipe, the mixture in the autoclave was cooled and water was added thereto. After the layer of light oil was separated, the water layer was subjected to acid separating to give 2-hydroxynaphthalene-6-carboxylic acid.

The yield and selective ratio of this carboxylic acid are shown in Table 1.

EXAMPLE 2

A reaction was made to take place in a one-liter autoclave, having a cooling pipe (300 cc) attached thereto, under conditions similar to those in Example 1.

The condensates were eliminated from the reaction system through an outlet in the lower part of the cooling pipe and the $CO_2$ exhausted was returned to the reaction system through an outlet in the upper part of the cooling pipe which led to the top of the autoclave.

The yield and selective ratio of 2-hydroxynaphthalene-6-carboxylic acid thereby obtained are shown in Table 1.

EXAMPLE 3

In a 50-liter autoclave were put 8.7 kg of β-naphthol, 22 kg of light oil, 7 kg of 48% caustic potash, and 0.9 kg of potassium carbonate and the contents were heated at 260° C. for five hours with stirring. After dehydration the reaction produced dehydrated β-naphtholpotassium. The light oil distillate was dehydrated and returned to the reaction system.

Next, the reaction temperature was raised to 265° C., and while the gases in the reaction system were exhausted therefrom at the rate of 4 Nm$^3$/hr and condensed in a cooling pipe (part of the light oil contained in the liquid condensate was returned to the reaction system after dried), the reaction system was replenished with $CO_2$ gas so as for the gas pressure therein to be maintained at 3.0 kg/cm$^2$ (G).

After the reaction was continued for six hours, the mixture obtained through the reaction was cooled to 100° C., and then water was added thereto and the mixture was separated. Unreacted β-naphthol was collected from the oil layer and the water layer was adjusted to pH value of 3.5 to precipitate 2-hydroxynaphthalene-6-carboxylic acid (the yield and selective ratio are shown in Table 1).

EXAMPLE 4

Two units of a 50 liter autoclave, No. 1 and No. 2, were put adjoining to each other, and β-naphtholpotassium dispersed in light oil, prepared in the same manner as in Example 3, was supplied to No. 1 autoclave at the rate of 8 kg/hr. The temperature of both the two autoclaves was adjusted to 269° C. and their $CO_2$ gas pressure was adjusted in such a manner as to be maintained at 2.9 kg/cm$^2$ (G), and while stirring was given so as for the β-naphtholpotassium, including $K_2CO_3$, not to settle. The reaction mixture was transferred from No. 1 autoclave into No. 2 autoclave through the connection pipe between No. 1 and No. 2 autoclave. In the autoclave $CO_2$ was dispersed from the bottom and was recycled after condensation of β-naphthol and water and the light oil in cooling pipe under 2.9 kg/cm$^2$ of $CO_2$ pressure and the reaction volumes of both autoclaves were maintained at contrast level with balance of feed rate to No. 1 autoclave and outlet from No. 2 autoclave.

Next, the reaction liquor in No. 2 autoclave was continuously drawn out at the rate of 8 kg/hr, and by the same procedure as in Example 3. 2-hydroxynaphthalene-6-carboxylic acid was obtained (the yield and selective ratio are shown in Table 1).

EXAMPLES 5-8

Except for the reaction temperatures which were 255° C. (Example 5), 265° C. (Example 6), 270° C. (Example 7) and 280° C. (Example β), the same conditions as in Example 2 were applied to the tests and 2-hydroxynaphthalene-6-carboxylic acid was obtained at the yields and selective ratios shown in Table 1.

EXAMPLES 9-11

Except for a reaction temperature of 270° C. (applied to the three tests) and reaction pressures of 2 kg/cm$^2$ (G) (Example 9), 8 kg/cm$^2$ (G) (Example 10), and 4 kg/cm$^2$ (G) (Example 11), the same conditions as in Example 2 were applied to the tests and 2-hydroxynaphthalene-6-carboxylic acid was obtained at the yields and selective ratios shown in Table 1.

EXAMPLES 12 and 13

The same conditions as in Example 2 were applied to the tests, except that, in Example 12 three times as much light oil in weight as β-naphtholpotassium was used, $K_2CO_3$ was made to have a molar ratio of 1.3 against β-naphtholpotassium, and the reaction was continued for 6 hours, and in Example 13 as much light oil in weight as β-naphtholpotassium was used, the potassium carbonate was made to have a molar ratio of 1.3 against β-naphtholpotassium, and the reaction was continued for eight hours. 2-Hydroxynaphthalene-6-carboxylic acid was obtained at the yields and selective ratios shown in Table 1.

COMPARATIVE EXAMPLE 1

From 84 grams of β-naphthol as the starting material β-naphtholpotassium was prepared by an ordinary method and dehydrated with both 1- and 2-isopropylnaphthalene as mediums. The 1- and 2-isopropylnaphthalene obtained as distillates from the dehydration were mixed with dehydrated β-naphtholpotassium.

This reaction liquor was put in an autoclave and made to undergo a reaction at a temperature of 265° C., under a $CO_2$ gas pressure of 3 kg/cm$^2$ (G), and for 16 hours. 2-Hydroxynaphthalene-6-carboxylic acid was obtained at the yield and selective ratio shown in Table 1.

COMPARATIVE EXAMPLE 2

β-Naphthol was treated with a 48 percent solution of potassium hydroxide (14.4 kg/hr), and the β-naphtholpotassium obtained was dispersed in light oil (18.2 kg/hr) and made to undergo a reaction under the same conditions as in Example 4 (no cooling pipe was attached; β-naphthol, moved by the overflow of the light oil, was eliminated from the reaction system through No. 2 autoclave).

2-Hydroxynaphthalene-6-carboxylic acid was obtained at the yield and selective ratio shown in Table 1.

COMPARATIVE EXAMPLE 3

The reaction in autoclave was carried out in the same manner as in Example 1, excepting that $CO_2$ gas was not exhausted from autoclave through reaction, and β-naphthol and water were not eliminated.

TABLE 1

|  |  | Yield (%) | Selection ratio (%) (*) |
|---|---|---|---|
| Example | 1 | 52 | 98.0 |
|  | 2 | 51 | 99 |
|  | 3 | 53 | 99.2 |
|  | 4 | 56 | 99.5 |
|  | 5 | 30 | 96 |
|  | 6 | 51 | 99 |
|  | 7 | 52 | 98.5 |
|  | 8 | 51 | 97 |
|  | 9 | 32 | 85 |
|  | 10 | 40 | 96 |
|  | 11 | 52 | 99 |
|  | 12 | 56 | 99.5 |
|  | 13 | 49 | 99.0 |
| Comparative | 1 | 27 | 90 |
| Example | 2 | 43 | 94 |
|  | 3 | 30 | 89.6 |

(*) (2-hydroxynaphthalene-6-carboxylic acid) × 100/[(2-hydroxynaphthalene-6-carboxylic acid) + (2-hydroxynaphthalene-3-carboxylic acid)]

What is claimed is:

1. A process for the preparation of 2-hydroxynaphthalene-6-carboxylic acid by reacting substantially anhydrous potassium beta-naphtholate with carbon dioxide in a reaction vessel and in the presence of a reaction medium that does not substantially dissolve the potassium beta-naphtholate to give 2-hydroxynaphthalene-6-carboxylic acid, the improvement which comprises dispersing said carbon dioxide during the reaction into the reaction mixture through a blow nozzle and removing beta-naphthol and water in the vapor phase along with the outgoing carbon dioxide gas.

2. The process of claim 1, wherein said carbon dioxide is continuously dispersed into said reaction mixture and said beta-naphthol, water and carbon dioxide are continuously removed from said reaction vessel.

3. The process of claim 1, wherein said removed beta-naphthol, water and carbon dioxide are thereafter cooled in the beta-naphthol and water are separated from the carbon dioxide by condensation to give recovered carbon dioxide.

4. The process of claim 3, wherein said recovered carbon dioxide is circulated back into the reaction vessel.

5. The process of claim 4, wherein said recovered carbon dioxide is recirculated back into the reaction mixture by dispersal through a blow nozzle.

6. The process of claim 4, wherein said reaction medium has a specific gravity of from 0.6 to 1.5.

7. The process of claim 1, wherein said reaction medium has a boiling point in the range of 150° C. to 400° C.

8. The process of claim 1, wherein said reaction medium is selected from the group consisting of an aliphatic hydrocarbon, an alicyclic hydrocarbon, an aromatic hydrocarbon, and an ether containing residual hydrocarbon groups.

* * * * *